United States Patent
Sommer

(10) Patent No.: US 7,217,318 B2
(45) Date of Patent: May 15, 2007

(54) NACREOUS PIGMENT AND METHOD FOR THE MANUFACTURE THEREOF

(75) Inventor: Günter Sommer, Hersbruck (DE)

(73) Assignee: Eckart GmbH & Co. KG, Fürth (DE)

( * ) Notice: Subject to any disclaimer, the term of this patent is extended or adjusted under 35 U.S.C. 154(b) by 0 days.

(21) Appl. No.: 10/900,226

(22) Filed: Jul. 28, 2004

(65) Prior Publication Data

US 2004/0261661 A1 Dec. 30, 2004

Related U.S. Application Data

(60) Division of application No. 10/203,012, filed on Aug. 5, 2002, now abandoned, which is a continuation-in-part of application No. PCT/EP01/00988, filed on Jan. 31, 2001.

(30) Foreign Application Priority Data

Feb. 4, 2000 (DE) ............................... 100 04 888

(51) Int. Cl.
 C23C 20/06 (2006.01)
 C23C 18/00 (2006.01)
 C09C 1/00 (2006.01)

(52) U.S. Cl. ............... 106/415; 427/215; 427/217; 427/331; 106/482; 106/457; 106/454; 106/450; 106/446; 106/431

(58) Field of Classification Search ........ 106/403–4, 106/425, 430, 431, 436, 438, 442, 453, 456; 427/215, 217, 218, 248

See application file for complete search history.

(56) References Cited

U.S. PATENT DOCUMENTS

| | | | |
|---|---|---|---|
| 3,123,490 A | | 3/1964 | Bolomey et al. |
| 3,438,766 A | | 4/1969 | Hanke |
| 5,135,812 A | | 8/1992 | Phillips et al. |
| 5,658,976 A | * | 8/1997 | Carpenter et al. .......... 524/403 |
| 6,270,840 B1 | * | 8/2001 | Weinert ...................... 427/251 |

FOREIGN PATENT DOCUMENTS

| | | |
|---|---|---|
| DE | 1 136 042 | 9/1962 |
| DE | 1 242 778 | 6/1967 |
| DE | 36 85 566 T2 | 12/1992 |
| DE | 42 12 119 A1 | 10/1993 |
| DE | 196 14 637 A1 | 10/1997 |
| DE | 198 17 286 A1 | 10/1999 |
| DE | 198 20 225 A1 | 11/1999 |
| DE | 198 22 046 A1 | 11/1999 |
| EP | 0 353 060 B1 | 9/1994 |
| EP | 0 990 715 A1 | 4/2000 |
| EP | 0 803 549 B1 | 9/2001 |
| WO | WO 93/08237 | 1/1992 |
| WO | WO 93/08237 * | 4/1993 |
| WO | WO 98/38254 | 2/1998 |
| WO | WO 98/13426 * | 4/1998 |
| WO | WO 00/43565 | 1/2000 |

OTHER PUBLICATIONS

European Patent Office, Patent Abstracts of Japan: Abstract for JP 01054071, "Pigment Having Thin Functional Coating Film", Nisshin Steel Co Ltd, Mar. 1, 1989.
Patent Abstracts of Japan, Publication No. JP 01054071, Publication Date: Jan. 3, 1989, Application Date: May 18, 1988, Applicant: Nisshin Steel Co Ltd, Inventor: Takatsu Kiyoshi, Title: "Pigment Having Thin Functional Coating Film".
Gerhard Pfaff et al. "Angle-Dependent Optical Effects Deriving from Submicron Structures of Films and Pigments" Chem. Rev 1999, Published on Web Jun. 11, 1999.

* cited by examiner

Primary Examiner—C. Melissa Koslow
(74) Attorney, Agent, or Firm—Browdy and Neimark, PLLC

(57) ABSTRACT

In a method for the manufacture of a nacreous pigment, in which a multi-layer film is produced by vacuum evaporation coating on a substrate and, after release from the substrate, the particles thus produced are comminuted to pigment particles of a desired size, vapor deposition of a plurality of layers taking place at separate locations within an evacuable container and the substrate being passed along the sources of evaporation, it is provided that at least a backing (A), in particular a silicon oxide layer, and at least a metal oxide layer (B), in particular a titanium oxide layer, are vapor-deposited on the substrate, in particular a circulating metal belt.

5 Claims, No Drawings

NACREOUS PIGMENT AND METHOD FOR THE MANUFACTURE THEREOF

This application is a division of Ser. No. 10/203,012 filed Aug. 5, 2002 now abandoned which is a 371 of PCT/EP01/00988 filed Jan. 31, 2001.

The invention relates to a nacreous pigment and a method for the manufacture thereof, in which a multilayer film is produced by vacuum evaporation coating on a substrate and, after release from the substrate, the particles thus produced are comminuted into pigment particles of the desired size, vapor deposition of a plurality of layers taking place at separate locations within an evacuable container and the substrate being passed along the sources of evaporation. Depending on the layer structure, interference phenomena may occur in pigments of the generic type.

Nacreous pigments are used in lots of fields of application, in particular for decorative purposes, car paints, cosmetic purposes or in the field of safety printing.

In known manufacturing processes, an inorganic salt, for example sodium chloride, is applied on the surface of the substrate as an intermediate layer that ensures subsequent detachment from the substrate, with several layers then being deposited by CVD or PVD coating and the multiple layered compound, after leaving the vacuum area, being detached in the form of individual particles by water dissolution.

An apparatus for putting into practice a method of the generic type in which a circulating metal belt is employed as a substrate, is known from German patent application 199 02 141, which is no prior publication. It specifies, by vapor deposition, to produce a reflecting or substrate layer of aluminum, on which, by subsequent evaporation, to deposit a transparent layer, for instance of magnesium fluoride or titanium oxide.

DE 12 42 778 provides that the vapor-deposited layers consist of the group of zinc sulfide, zinc oxide, guanine, magnesium fluoride, titanium dioxide, calcium fluoride and cryolite, with a material from the group of alkali halides, alkaline earth halides or alkali borates, such as $Na_2B_4O_7$; $B_2O_3$; $MgCl_2$, being used as a substrate for these films.

Evaporation temperatures depend on the respective chromogenic substance or substrate.

Interference phenomena are employed for chromogenic purposes by exploitation of the path difference of the light waves that is determined by reflection on the interfaces produced by the various deposited layers. These effects of interference are affected by the thickness of the individual layers and the index of refraction thereof. In the case of an uncolored pearlescent pigment, the product of film thickness in nm and refractive index is to remain within a range between 10 and 200.

Interference colors are produced when this product is in a range above 200, the brightest colors occurring with a given pigment weight concentration in the range of 200 to approximately 1500. Color intensity also depends on the uniformity of platelet thickness i.e., on the plane parallelism of the substrate and the plane parallelism of the deposited layers, because pigment platelets of irregular thickness reflect varying colors which may cancel one another so that there is no color effect or no production of pure colors.

A summary of the current prior art is to be found in Chem. Rev. 1999, 99, pages 1963 to 1981, which illustrates that maximal reflection shifts to shorter wave lengths as the angle of view grows. Correspondingly, a thin film with incident white light can show colors that change along the entire spectrum of visible light from red to blue as a viewer's angle of view becomes flatter. It is also shown mathematically that greater variance of thickness results in less defined colors, which is the case for example with natural mica used as a substrate. Correspondingly, individual particles exhibit interference phenomena, which is not the case with an arrangement of several particles. The optical characteristics of such a natural mica based arrangement are nearly the same as those of an individual metal oxide layer, in particular a $TiO_2$ layer. As compared to this, more recently used pearlescent luster pigments on the basis of artificially produced aluminum oxide and silicon oxide substrates have a constant thickness, thus becoming part of the optical system. Multilayer oxide coatings on the basis of $SiO_2$ substrates exhibit stronger and brighter interference colors than is the case with mica as a substrate.

Liquid-phase or gas-phase precipitation leads to significant porosity, frequently of more than 25 percent of the layer. This porosity lessens the intensity of the reflected light.

As for the production of inorganic films, vacuum evaporation coating—also using electron beams—sputtering and the CVD method are specified as methods known per se. However, these methods are mentioned to be rather costly and therefore used only for optical lenses, filters and the like.

As for the production of $TiO_2$ flakes, continuous film fragmentation is mentioned as a familiar method, the films being produced for instance by thermal hydrolysis of $TiOCl_2$. Alternatives consist in the deposition of titanium alkoxide on a surface and fragmentation of the resulting film by vapor treatment, in depositing colloidal $TiO_2$ solution on a glass surface and scratching off the resulting film. Mention is also made of the application of a $TiOCl_2$ solution on a gelatin film and detachment of the gelatin film, vacuum deposition, acid treatment of potassium titanate and subsequent heating, or the production and fragmentation of hollow $TiO_2$ particles from a mix of a surfactant with a colloidal $TiO_2$ solution. Substrate-free $TiO_2$ flakes may also be obtained by the substrates being dissolved in strong acids or bases.

In the production of $TiO_2$ coated mica from a $TiOCl_2$ solution, attention must be paid to the reactor geometry and the mixing conditions. The $TiO_2$ layers obtained may be coated with organic dyes as well as with thin layers of silver, nickel or compositions of various metals in order to obtain a darker shade.

DE-AS 1 136 042 teaches to use substrates of a low refraction index in the form of oxides or oxide hydrates of metals of the IVth and/or Vth group, for example $SiO_2$, and to coat them with substances of a higher refraction index, for example oxides of Ti, Fe, Sb, Sn etc.

The production of the platelets there described is implemented by a glass, ceramic, metal or plastic substrate being wetted with a solution of a hydrolysable compound of the metal that is to be converted into the desired oxide; from the liquid film thus produced, the respective oxide or oxide hydrate is formed as a thin coating by subsequent heating.

U.S. Pat. No. 3,438,796 teaches to produce pigment platelets that consist of a plurality of films of silicon oxide and aluminum, with the silicon film serving as a protective layer for the aluminum on the one hand and for producing interference effects in dependence on its thickness on the other. The aluminum film may be adjusted in thickness so that it is substantially impermeable to light. The layers are produced by chargewise vapor deposition.

EP 0 803 549 provides silicon oxide layers to be vapor-deposited on conventional platelet particles of a length of for instance 1 to 200 μm. The platelets must consist of a metallically reflecting material or metal alloys. Alternatively, the use of mica may be considered. It further specifies that it is a familiar way of proceeding to deposit, on such a substrate of a colorless oxide, crystallized titanium oxide layers, for instance in the form of rutile, on which to deposit another layer of colored inorganic material such as iron oxide.

Earlier studies have shown that the refraction index and absorption of vapor-deposited silicon oxide layers are the lower, the slower evaporation takes place and the greater the oxygen content, so that there is the possibility to manipulate the optical properties during vapor deposition.

By subsequent treatment or subsequent coating, all the pigments described above are stabilized towards weather factors and light.

Proceeding from this, it is the object of the invention to embody a method for the manufacture of a nacreous pigment and a nacreous pigment that can be manufactured at a high production rate and excels by excellent durability properties and a wide range of possible colors accompanied with high color saturation and opacity.

According to the invention this object is attained by at least one backing layer, in particular a silicon oxide backing layer, and at least one metal oxide layer, in particular a titanium oxide layer being vapor-deposited on the substrate, in particular a circulating metal belt.

The silicon oxide layer thus deposited helps create a backing which, after being peeled off the substrate, namely the metal belt, excels by high plane parallelism and defined thickness in particular as compared to natural mica platelets, but also to platelets produced by wet-processing.

As opposed to natural mica, the SiO starting material used according to the invention does not have any impurities, for instance iron. Further, there is no need of complicated preparation such as calcination, comminution, grading etc.

Due to its simple way of manufacture, the backing according to the invention also has advantages over synthetic mica (phlogopite), which has never gained any commercial importance because of complicated manufacturing requirements at high pressure and elevated temperature.

The vapor deposition rate and oxygen partial pressure help regulate the optical properties such as the refraction index and reflection coefficient of the backing, it being possible in this way to produce defined and reproducible shades and changes of color in dependence on the angle of view.

The thickness of the layer that is vapor-deposited subsequently, in particular a titanium oxide layer, can also be regulated as desired through the vapor deposition rate and/or the metal belt velocity, possessing excellent plane parallelism due to the plane surface of the previously deposited silicon oxide layer.

As opposed to pearlescent pigments coated by wet chemical deposition, the pigments produced according to the invention are plane parallel as far as to the outer edge. The result is higher color purity and improved luster even in minor particles, because the scattered-edge portion is minimized.

There are no secondary precipitations as they occur in wet chemical processes. Further, there are virtually no crystal germs as a basis for crystal growth, because the substrate has a very low porosity and a smooth surface.

As a result of the manufacturing method according to the invention, the pigment platelets peeled off the backing have largely identical and reproducible optical properties, for example the same shade of color when viewed from a certain angle.

The pigments obtained according to the invention have great shear stability. This is due to the fact that excellent bonding of the SiO and TiO layers is obtained by the method according to the invention. As compared to this, the shear stability of natural-mica-based pigments is rather bad due to the layered structure thereof and the morphology of the metal oxide layer.

The thickness of both layers is easy to regulate, in particular as compared to the hydrolysis belt method (shrinking of the deposited layer), and the color can be influenced in this way, with the thickness of the SiO layer influencing the color even stronger than the thickness of the TiO layer.

In the method according to the invention, there is no waste of film and, correspondingly, no need of costly waste disposal. According to the invention, it is conceivable to use substances that have a high evaporation temperature, such as TiO, which would not be possible in conventional methods that use a plastic film, because of the lack of temperature resistance of these films.

In as much as the term layer sequence is mentioned above or in the following, this implies protection also of the reverse layer sequence because, once the platelets are peeled off the substrate, the orientation originally given by the substrate does no longer exist.

In keeping with the invention, provision can be made for the backing to be enclosed on both sides by metal oxide layers of varying thickness (asymmetric layer structure). Of course, such a layer structure cannot be obtained by wet chemical processes. As the pigments, when they are worked into paint and when an object is painted, will be located substantially parallel to the painted surface, varying thickness of the metal oxide layers will result in that, randomly distributed, either the thicker or thinner metal oxide layer is on top, which helps create colors and paints of novel interference effects.

Provision may further be made for another metal layer, in particular an aluminum layer, to be vapor-deposited on a three-layered arrangement as described above, it being possible to obtain strong opacity of these pigments by a correspondingly adjusted layer thickness. In a manner known per se, a comparatively thin silicon oxide layer may be vapor-deposited as a protective layer on the aluminum layer.

In keeping with another embodiment, it is provided that a metal oxide layer and the backing layer are followed by a metal layer, a silicon oxide layer and another metal oxide layer, the metal layer being aluminum, chromium, gold, copper, silver or the like.

In keeping with another embodiment, it is provided that the metal oxide layer and the backing are followed by a metal layer, the metal again being aluminum, chromium, gold, copper, silver or the like.

The thickness of the backing preferably ranges between 20 and 1000 nm, the thickness of the metal oxide layer preferably ranges between 20 and 500 nm and that of the metal layer preferably between 40 and 60 nm.

The above-specified pigments according to the invention may have further layers of their surface, for example for increased weathering resistance. These layers can be applied by wet chemical or PVD processes ("inline").

Suitable substances may be selected from the group of oxides and/or oxyhydrates and/or hydroxides of aluminum, silicon, zirconium, phosphor, boron, zinc, cerium, manganese, chromium, molybdenum, iron and tin. The mentioned stabilizing substances may also be incorporated as a doping agent in the outermost layers.

In keeping with the method according to the invention, it is provided that first a backing is produced by vacuum evaporation coating of a circulating metal belt; and that, after parting from the substrate, the backing particles thus produced are comminuted to a desired size, these backing particles then being equipped with at least one layer by wet coating. Use is made in particular of the fundamental advantage, specified above, of backing particles that are precipitated on a metal substrate and the subsequent coating can then be put into practice by familiar wet coating techniques. The backing may consist in particular of silicon oxide, silicate, boron oxide, borates, aluminum oxide, aluminates, titanium boride or mixtures thereof.

Provision may further be made for the backing particles to comprise network formers or network modifiers and/or barium sulfate for surface smoothing and/or soluble or insoluble inorganic or organic colorants.

The layers applied by wet chemical deposition may advantageously consist of oxides of the metals zirconium, chromium, titanium, iron, zinc, oxide hydrates of these metals, ferrotitanates, titanium suboxides or mixtures thereof, it being possible to reduce the metal oxides. In a manner known per se, additional coatings may be applied for light stabilization and weathering resistance.

Another embodiment of the method according to the invention relates to the manufacture of single-layer nacreous pigments, wherein—apart from light stabilization and weathering resistance coatings that might be provided—a single, optically active layer of titanium oxide, iron oxide, titanium suboxides, titanium oxinitrides, molybdenum sulfide or ferrotitanium oxide is vacuum-deposited on a circulating metal belt. Such single-layer structures preferably have an optically active layer of a thickness in the order of magnitude of 20 to 500 nm, preferably 40 to 100 nm. These single-layer structures excel in color brightness and purity. Putting them into practice has so far failed due to lacking shear stability, which can however be obtained by the process according to the invention.

Another embodiment of the method according to the invention relates to the manufacture of nacreous pigments from a metal oxide layer, in particular a titanium oxide layer, a metal layer and another metal oxide layer, in particular a titanium oxide layer, by vacuum evaporation coating on a circulating metal belt. The metal may be aluminum, chromium, gold, copper, silver or the like.

In order for the coating to be parted from the substrate more easily, a release coat may be applied, consisting of a paint, a salt, a salty compound or an organic material. Precipitation of this release coat may for instance take place by painting or evaporation.

The invention also relates to a nacreous pigment manufactured in accordance with one of the described methods as well as to paints, lacquers, cosmetics and plastics that comprise these nacreous pigments, and the use of these nacreous pigments for the production of paints, lacquers, cosmetics and plastics.

Details of the invention will become apparent from the ensuing description of exemplary embodiments.

EXAMPLE 1

A release layer of a water soluble salt that is indecomposably high-vacuum evaporable is applied by vacuum ($10^{-4}$ mbar) evaporation coating on a circulating metal belt, which is followed by a TiO layer, an SiO layer and another TiO layer.

The belt circulation speed is 2 m/s, the temperature of the TiO sources is 2200° C., the temperature of the SiO source 1450° C. The distance of the evaporation sources from each other is 17 cm.

The optical thickness of the SiO layer is 202 nm, that of the TiO layers 198 nm.

After being parted from the metal belt in a water bath, the film is stirred by a high-speed stirrer and comminuted into pigment particles of a size of 1 to 100 μm.

The powder obtained has a blue color.

EXAMPLE 2

A release layer of a water soluble salt that is indecomposably high-vacuum evaporable is applied by vacuum ($10^{-4}$ mbar) evaporation coating on a circulating metal belt, which is followed by a TiO layer, an aluminum layer and another TiO layer.

The belt circulation speed is 2 m/s, the temperature of the TiO sources is 2200° C., the temperature of the aluminum source 650° C. The distance of the evaporation sources from each other is 17 cm.

The optical thickness of the aluminum layer is 245 nm, that of the TiO layers 603 nm.

After being parted from the metal belt in a water bath, the film is stirred by a high-speed stirrer and comminuted into pigment particles of a size of 1 to 100 μm.

The powder obtained has a light blue color of metallic character and nacreous luster.

EXAMPLE 3

A release layer of a water soluble salt that is indecomposably high-vacuum evaporable is applied by vacuum ($10^{-4}$ mbar) evaporation coating on a circulating metal belt, which is followed by a TiO layer.

The belt circulation speed is 2 m/s, the temperature of the TiO sources is 2200° C.

The optical thickness of the TiO layer is 500 nm.

After being parted from the metal belt in a water bath, the film is stirred by a high-speed stirrer and comminuted into pigment particles of a size of 1 to 100 μm.

The powder obtained has a reddish yellow color.

EXAMPLE 4

A release layer of a water soluble salt that is indecomposably high-vacuum evaporable is applied by vacuum ($10^{-4}$ mbar) evaporation coating on a circulating metal belt, which is followed by an SiO layer.

The belt circulation speed is 2 m/s, the temperature of the SiO source is 1450° C.

The optical thickness of the SiO layer is 200 nm.

After being parted from the metal belt in a water bath, the film is stirred by a high-speed stirrer and comminuted into pigment particles of a size of 1 to 100 μm.

Subsequently, the powder obtained is coated in a known manner with titanium dioxide by wet chemical treatment.

Depending on layer thickness, pigments of varying interference colors are obtained.

Measuring the optical layer thicknesses takes place by the quartz-crystal thin film monitoring method.

What is claimed is:

1. A method for the manufacture of a nacreous pigment, comprising first a backing of silicon oxide is produced by vacuum evaporation coating of a circulating metal belt and, after release from the substrate, the backing is comminuted to particles of a particle size of 1–100 microns, these backing particles subsequently are provided by wet coating with at least one layer, said at least one layer being an oxide of zirconium, chromium, titanium, iron or zinc, or an oxide hydrate thereof, or ferrotitanium, a ferrotitanate, a titanium suboxide or a mixture thereof.

2. A method according to claim 1, wherein the metal oxides are reduced.

3. A method according to claim 1 wherein additional coatings are applied for light stabilization and weathering resistance.

4. The method of claim 1 wherein said one layer comprises titanium dioxide.

5. A method for the manufacture of a nacreous pigment, comprising first a backing of silicon oxide is produced in a thickness of 20 to 1000 nm by vacuum evaporation coating of a circular metal belt, and after release from the substrate, the backing is comminuted to particles of a particle size from 1 to 100 microns, said backing particles subsequently being provided by wet coating with at least one another or second layer, wherein the at least one another or second layer applied by wet chemical deposition consists of an oxide of at least one of the metals zirconium, chromium, titanium, iron, zinc or oxide hydrates of these metals, ferrotitanium, a ferrotitanate, titanium suboxides or mixtures thereof.

* * * * *